United States Patent
Ross et al.

(10) Patent No.: US 9,053,534 B2
(45) Date of Patent: Jun. 9, 2015

(54) VOXEL-BASED APPROACH FOR DISEASE DETECTION AND EVOLUTION

(71) Applicant: THE REGENTS OF THE UNIVERSITY OF MICHIGAN, Ann Arbor, MI (US)

(72) Inventors: Brian D. Ross, Ann Arbor, MI (US); Thomas L. Chenevert, Ann Arbor, MI (US); Craig Galban, Ann Arbor, MI (US); Benjamin Lemasson, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 13/683,746

(22) Filed: Nov. 21, 2012

(65) Prior Publication Data
US 2013/0129168 A1    May 23, 2013

Related U.S. Application Data

(60) Provisional application No. 61/563,333, filed on Nov. 23, 2011.

(51) Int. Cl.
  *G06K 9/00* (2006.01)
  *G06T 7/00* (2006.01)
  (Continued)

(52) U.S. Cl.
  CPC .............. *G06T 7/0012* (2013.01); *A61B 5/742* (2013.01); *G06T 7/0016* (2013.01); *G06T 2207/10088* (2013.01); *G06T 2207/30016* (2013.01); *G06T 2207/30096* (2013.01); *A61B 5/055* (2013.01); *A61B 5/4842* (2013.01)

(58) Field of Classification Search
  None
  See application file for complete search history.

(56) References Cited

U.S. PATENT DOCUMENTS

| 6,163,152 A | 12/2000 | Bernstein et al. |
| 6,381,296 B1 | 4/2002 | Nishiura |
| 6,567,684 B1 | 5/2003 | Chenevert et al. |

(Continued)

FOREIGN PATENT DOCUMENTS

| WO | WO-01/56466 | 8/2001 |
| WO | WO-02/061457 | 8/2002 |

(Continued)

OTHER PUBLICATIONS

Dhermain, Frederic G., Peter Hau, Heinrich Lanfermann, Andreas H. Jacobs, and Martin J. van den Bent. "Advanced MRI and PET imaging for assessment of treatment response in patients with gliomas." The Lancet Neurology 9, No. 9 (Sep. 2010): 906-920.*

(Continued)

*Primary Examiner* — Sumati Lefkowitz
*Assistant Examiner* — Carol Wang
(74) *Attorney, Agent, or Firm* — Marshall, Gerstein & Borun LLP

(57) ABSTRACT

A voxel-based technique is provided for performing quantitative imaging and analysis of tissue image data. Serial image data is collected for tissue of interest at different states of the issue. The collected image data may be normalized, after which the registered image data is analyzed on a voxel-by-voxel basis, thereby retaining spatial information for the analysis. Various thresholds are applied to the registered tissue data to predict or determine the evolution of a disease state, such as brain cancer, for example.

16 Claims, 3 Drawing Sheets
(1 of 3 Drawing Sheet(s) Filed in Color)

(51) Int. Cl.
  *A61B 5/00* (2006.01)
  *A61B 5/055* (2006.01)

(56) References Cited

U.S. PATENT DOCUMENTS

| | | | |
|---|---|---|---|
| 6,579,240 | B2 | 6/2003 | Bjaerum et al. |
| 6,845,342 | B1 | 1/2005 | Basser et al. |
| 6,901,277 | B2 | 5/2005 | Kaufman et al. |
| 6,969,991 | B2 | 11/2005 | Bammer et al. |
| 7,078,897 | B2 | 7/2006 | Yablonskiy et al. |
| 1,000,940 | A1 | 1/2011 | Rewcastle et al. |
| 7,897,792 | B2 | 3/2011 | Iikura et al. |
| 7,949,164 | B2 | 5/2011 | Degani et al. |
| 8,185,186 | B2 | 5/2012 | Ross et al. |
| 2003/0018245 | A1 | 1/2003 | Kaufman et al. |
| 2003/0065260 | A1 | 4/2003 | Cheng et al. |
| 2004/0254444 | A1* | 12/2004 | Bittner .................. 600/410 |
| 2005/0105788 | A1 | 5/2005 | Turek et al. |
| 2008/0021301 | A1 | 1/2008 | Gonzalez et al. |
| 2009/0035218 | A1* | 2/2009 | Ross et al. .................. 424/9.1 |
| 2009/0058417 | A1 | 3/2009 | Yanasak et al. |
| 2009/0234237 | A1 | 9/2009 | Ross et al. |
| 2010/0249099 | A1 | 9/2010 | Rewcastle et al. |
| 2010/0254584 | A1* | 10/2010 | Gulsun et al. .................. 382/131 |
| 2011/0053907 | A1 | 3/2011 | Rewcastle et al. |
| 2011/0066024 | A1 | 3/2011 | Shih et al. |
| 2011/0077503 | A1 | 3/2011 | Bonilha et al. |
| 2011/0187367 | A1 | 8/2011 | Feiweier et al. |
| 2012/0316422 | A1 | 12/2012 | Ross et al. |
| 2013/0004043 | A1 | 1/2013 | Ross et al. |
| 2013/0004044 | A1 | 1/2013 | Ross et al. |

FOREIGN PATENT DOCUMENTS

| | | |
|---|---|---|
| WO | WO-2008/122056 A2 | 10/2008 |
| WO | WO-2008/154741 | 12/2008 |
| WO | WO-2010/116124 | 10/2010 |
| WO | WO-2011/137370 A2 | 11/2011 |
| WO | WO-2013/003826 | 1/2013 |
| WO | WO-2013/006506 | 1/2013 |

OTHER PUBLICATIONS

Vilanova, Joan C., and Joaquim Barceló. "Diffusion-weighted whole-body MR screening." European journal of radiology 67, No. 3 (Sep. 2008): 440-447.*

Sawlani, Rahul N., Jeffrey Raizer, Sandra W. Horowitz, Wanyong Shin, Sean A. Grimm, James P. Chandler, Robert Levy, Christopher Getch, and Timothy J. Carroll. "Glioblastoma: a method for predicting response to antiangiogenic chemotherapy by using MR perfusion imaging-pilot study." Radiology 255, No. 2 (May 2010): 622.*

Tsien, Christina, Craig J. Galbán, Thomas L. Chenevert, Timothy D. Johnson, Daniel A. Hamstra, Pia C. Sundgren, Larry Junck et al. "Parametric response map as an imaging biomarker to distinguish progression from pseudoprogression in high-grade glioma." Journal of Clinical Oncology 28, No. 13 (May 1, 2010): 2293-2299.*

Galbán, Craig J., Thomas L. Chenevert, Charles R. Meyer, Christina Tsien, Theodore S. Lawrence, Daniel A. Hamstra, Larry Junck et al. "The parametric response map is an imaging biomarker for early cancer treatment outcome." Nature medicine 15, No. 5 (May 2009): 572-576.*

Zacharaki, Evangelia I., Dinggang Shen, Seung-Koo Lee, and Christos Davatzikos. "ORBIT: a multiresolution framework for deformable registration of brain tumor images." Medical Imaging, IEEE Transactions on 27, No. 8 (2008): 1003-1017.*

Bagrodia et al., Mechanisms of intrinsic and acquired resistance to kinase-targeted therapies, Pigment Cell Melanoma Res., 25(6):819-31 (2012).

Baines et al., Inhibition of Ras for cancer treatment: the search continues, Future Med. Chem., 3(14):1787-808 (2011).

Bammer et al., Analysis and generalized correction of the effect of spatial gradient field distortions in diffusion weighted imaging, Magn. Res. Med, 50:560-9 (2003).

Bammer et al., Assessment of spatial gradient field distortion in diffusion-weighted imaging, ISMRM Proceedings (2002).

Besil et al., A method for registration of 3-D shapes, IEEE Trans. Pattern Analysis and Machine Intelligence, 14(2):239-56 (1992).

Bing et al., Voxel-by-voxel functional diffusion mapping for early evaluation of breast cancer treatment, Information Processing in Medical Imaging, pp. 276-287 (2009).

Bookstein et al., Principal Warps: Thin-plate splines and the decomposition of deformations, IEEE Transactions on Pattern Analysis and Machine Intelligence, 11(6):567-85 (1989).

Breen et al., Three-dimensional method for comparing in vivo interventional MR images of thermally ablated tissue with tissue response, J. Magn. Reson. Imaging, 18(1):90-102 (2003).

Brix et al., Microcirculation and microvasculature in breast tumors: pharmacokinetics analysis of dynamic MR image series, Mag. Reson. Med., 52:420-9 (2004).

Brix et al., Pharmacokinetic parameters in CNS Gd-DTPA enhanced MR imaging, J. Comput Assist. Tomogr., 15:621-8 (1991).

Bubley et al., Eligibility and response guidelines for phase II clinical trials in androgen-independent prostate cancer: recommendations from the Prostate-Specific Antigen Working Group, J. Clin. Oncol., 17(11):3461-7 (1999).

Bulinski et al., Overexpression of MAP4 inhibits organelle motility and trafficking in vivo, J. Cell Sci., 110(Pt. 4):3055-64 (1997).

Cao et al., Survival prediction in high-grade gliomas by MRI perfusion before and during early stage of RT, Int. J. Radiat. Oncol. Biol. Phys., 64:876-85 (2006).

Carracedo et al., Inhibition of mTORC1 leads to MAPK pathway activation through a PI3K-dependent feedback loop in human cancer, J. Clin Invest., 118(9):3065-74 (2008).

Castellano et al., RAS Interaction with PI3K: More Than Just Another Effector Pathway, Genes Cancer, 2(3):261-74 (2011).

Chan et al., Survival and failure patterns of high-grade gliomas after three-dimensional conformal radiotherapy, J. Clin. Oncol., 20:1635-42 (2002).

Chenevert et al., Diffusion coefficient measurement using a temperature-controlled fluid for quality control in multicenter studies, J. Magn. Reson. Imaging, 34(4):983-7 (2011).

Chenevert et al., Diffusion magnetic resonance imaging: an early surrogate marker of therapeutic efficacy in brain tumors, J. Natl. Cancer Inst., 92(24):2029-36 (2000).

Chenevert et al., Diffusion MRI: a new strategy for assessment of cancer therapeutic efficacy, Mol. Imaging, 1(4):336-43 (2002).

Chenevert et al., Icewater for quality control of diffusion measurements in multi-center trials, in Proceedings of the 19th Annual Meeting of ISMRM, Montreal, Quebec, Canada, p. 912 (2011).

Chenevert et al., Monitoring early response of experimental brain tumors to therapy using diffusion magnetic resonance imaging, Clin. Cancer Res., 3(9):1457-66 (1997).

Collignon et al., 3D multi-modality medical image registration using feature space clustering, Lecture Notes in Computer Science, 905:195-204 (1995).

Degani, Mapping pathophysiological features of breast tumors by MRI at high spatial resolution, Nat. Med., 3:780-2 (1997).

Early Breast Cancer Trialists Collaborative Group, Polychemotherapy for early breast cancer: an overview of the randomised trials, The Lancet, 352:930-42 (1998).

Eda et al., The relations between expiratory chest CT using helical CT and pulmonary function tests in emphysema, Am. J. Respir. Crit Care Med., 155(4):1290-4 (1997).

Ellingson et al., Volumetric analysis of functional diffusion maps is a predictive imaging biomarker for cytotoxic and anti-angiogenic treatments in malignant gliomas, J. Neuro-Oncol., 102(1):95-103 (2010).

Engelman et al., Effective use of PI3K and MEK inhibitors to treat mutant Kras G12D and PIK3CA H1047R murine lung cancers, Nat. Med., 14(12):1351-6 (2008).

Evelhoch et al., Applications of magnetic resonance in model systems: cancer therapeutics, Neoplasia, 2(1-2):152-65 (2000).

Eyal et al., Model-based and model-free parametric analysis of breast dynamic-contrast-enahnced MRI, NMR Biomed., 22:40-53 (2007).

(56) References Cited

OTHER PUBLICATIONS

Falchook et al., Activity of the oral MEK inhibitor trametinib in patients with advanced melanoma: a phase 1 dose-escalation trial, Lancet Oncol., 13(8):782-9 (2012).

Fogelman et al., Positron emission tomography and bone metastases, Semin. Nucl. Med., 35(2):135-42 (2005).

Galban et al., A feasibility study of parametric response map analysis of diffusion-weighted magnetic resonance imaging scans of head and neck cancer patients for providing early detection of therapeutic efficacy, Translational Oncol., 2:184-90 (2009).

Galban et al., Prospective analysis of parametric response map-derived MRI biomarkers: identification of early and distinct glioma response patterns not predicted by standard radiographic assessment, Clin. Cancer Res., 17(14):4751-60 (2011).

Galbraith et al., Reproducibility of dynamic contrast-enhanced MRI in human muscle and tumours: comparison of quantitative and semi-quantitative analysis, NMR Biomed., 15:132-42 (2002).

Galons et al., Early increases in breast tumor xenograft water mobility in response to paclitaxel therapy detected by non-invasive diffusion magnetic resonance imaging, Neoplasia, 1(2):113-7 (1999).

Gevenois et al., Comparison of computed density and macroscopic morphometry in pulmonary emphysema, Am. J. Respir. Crit. Care Med., 152(2):653-7 (1995).

Gevenois et al., Comparison of computed density and microscopic morphometry in pulmonary emphysema, Am. J. Respir. Crit. Care Med., 154(1):187-92 (1996).

Gorbunova et al., Early detection of emphysema progression, Med. Image Comput. Comput. Assist. Interv., 13(Pt. 2):193-200 (2010).

Gorbunova et al., Weight preserving image registration for monitoring disease progression in lung CT, Medical Image Computing and Computer-Assisted Intervention A MICCAI 2008, pp. 863-870 (2008).

Green et al., Multi-scale rigid registration to detect damage in micro-CT images of progressively loaded bones, 2011 8th IEEE International Symposium on Biomedical Imaging: From Nano to Micro, IEEE, pp. 1231-1234 (2011).

Hall et al., Therapeutic efficacy of DTI-015 using diffusion magnetic resonance imaging as an early surrogate marker, Clin. Cancer Res., 10(23):7852-9 (2004).

Hamaoka et al., Bone imaging in metastatic breast cancer, J. Clin. Oncol., 22(14):2942-53 (2004).

Hamstra et al., Evaluation of the functional diffusion map as an early biomarker of time-to-progression and overall survival in high-grade glioma, Proc. Natl. Acad. Sci. USA, 102(46):16759-64 (2005).

Hamstra et al., Functional diffusion map as an early imaging biomarker for high-grade glioma: correlation with conventional radiologic response and overall survival, J. Clin. Oncol., 26(20):3387-94 (2008).

Hamstra et al., The use of 19F spectroscopy and diffusion-weighted MRI to evaluate differences in gene-dependent enzyme prodrug therapies, Mol. Ther., 10(5):916-28 (2004).

Hatzivassiliou et al., RAF inhibitors prime wild-type RAF to activate the MAPK pathway and enhance growth, Nature, 464(7287):431-5 (2010).

Hayward et al., Assessment of response to therapy in advanced breast cancer (an amendment), Br. J. Cancer, 38(1):201 (1978).

Hayward et al., Assessment of response to therapy in advanced breast cancer, Br. J. Cancer, 35(3):292-8 (1977).

Helen et al., Segmentation of pulmonary parenchyma in CT lung images based on 2D Otsu optimized by PSO, Emerging Trends in Electrical and Computer Technology, 2011 International Conference on IEEE, pp. 536-541 (2011).

Hoffmann, Pharmacokinetic mapping of the breast: a new method for dynamic MR mammography, Magn. Reson. Med., 33:506-14 (1995).

Hogg et al., The nature of small-airway obstruction in chronic obstructive pulmonary disease, N. Engl. J. Med., 350(26):2645-53 (2004).

Hu et al., Automatic lung segmentation for accurate quantitation of volumetric X-ray CT images, IEEE Trans. Med. Imaging, 20(6):490-8 (2001).

Hylton, Dynamic contrast-enhanced magnetic resonance imaging as an imaging biomarker, J. Clin. Oncol., 24:3293-8 (2006).

Infante et al., Safety, pharmacokinetic, pharmacodynamic, and efficacy data for the oral MEK inhibitor trametinib: a phase 1 dose-escalation trial, Lancet Oncol., 13(8):773-81 (2012).

International Search Report and Written Opinion, PCT/US2012/066338, mailing date Mar. 11, 2013.

Jacobs et al., Registration and warping of magnetic resonance images to histological sections, Med. Phys., 26(8):1568-78 (1999).

Janke et al., Use of spherical harmonic deconvolution methods to compensate for nonlinear gradient effects on MRI images, Magn. Reson. Med., 52(1):115-22 (2004).

Jemal et al., Cancer statistics, 2010, CA Cancer J. Clin., 60(5):277-300 (2010).

Jennings et al., Early response of prostate carcinoma xenografts to docetaxel chemotherapy monitored with diffusion MRI, Neoplasia, 4(3):255-62 (2002).

Jordan et al., Dynamic contrast-enhanced and diffusion MRI show rapid and dramatic changes in tumor microenvironment in response to inhibition of HIF-1alpha using PX-478, Neoplasia, 7(5):475-85 (2005).

Kalikin et al., In vivo visualization of metastatic prostate cancer and quantitation of disease progression in immunocompromised mice, Cancer Biol. Ther., 2(6):656-60 (2003).

Karreth et al., C-Raf inhibits MAPK activation and transformation by B-Raf(V600E), Mol. Cell, 36(3):477-86 (2009).

Kiessling et al., Contrast agents and applications to assess tumor angiogenesis in vivo by magnetic resonance imaging, Curr. Med. Chem., 14:77-91 (2007).

Kim et al., Correction of local deformations in fMRI by 3D nonlinear warping in map-slice-to-volume approach, Proc. Intl. Soc. Mag. Reson. Med., 8:1765 (2000).

Kim et al., CT metrics of airway disease and emphysema in severe COPD, Chest., 136(2):396-404 (2009).

Kim et al., Mutual information for automated unwarping of rat brain autoradiographs, Neuroimage, 5(1):31-40 (1997).

Kim et al., Phase II study of the MEK1/MEK2 inhibitor Trametinib in patients with metastatic BRAF-mutant cutaneous melanoma previously treated with or without a BRAF inhibitor, J. Clin. Oncol., 31(4):482-9 (2013).

Kubo et al., Expiratory and inspiratory chest computed tomography and pulmonary function tests in cigarette smokers, Eur. Respir. J., 13(2):252-6 (1999).

Latour et al., Time-dependent diffusion of water in a biological model system, Proc. Natl. Acad. Sci. USA, 91(4):1229-33 (1994).

Laun et al., How background noise shifts eigenvectors and increases eigenvalues in DTI, MAGMA, 22(3):151-8 (2009).

Lazebnik et al., Volume registration using needle paths and point landmarks for evaluation of interventional MRI treatments, IEEE Trans. Med. Imaging, 22(5):653-60 (2003).

Lee et al., A feasibility study evaluating the functional diffusion map as a predictive imaging biomarker for detection of treatment response in a patient with metastic prostate cancer to the bone, Neoplasia, 9(12):1003-11 (2007).

Lee et al., Dynamic imaging of emerging resistance during cancer therapy, Cancer Res., 66(9):4687-92 (2006).

Lee et al., Prospective early response imaging biomarker for neoadjuvant breast cancer chemotherapy, Clin. Cancer Res., 13(2 Pt. 1):443-50 (2007).

Leung et al., Automatic quantification of changes in bone in serial MR images of joints, IEEE Transactions on Medical Imaging, 25(12):1617-26 (2006).

Li et al., Pulmonary CT image registration and warping for tracking tissue deformation during the respiratory cycle through 3D consistent image registration, Med. Phys., 35(12):5575-83 (2008).

Lorusso et al., Phase I and pharmacodynamic study of the oral MEK inhibitor CI-1040 in patients with advanced malignancies, J. Clin. Oncol., 23(23):5281-93 (2005).

Low et al., Novel breathing motion model for radiotherapy, Int. J. Radiat. Oncol. Biol. Phys., 63(3):921-9 (2005).

Lyng et al., Measurement of cell density and necrotic fraction in human melanoma xenografts by diffusion weighted magnetic resonance imaging, Magn. Reson. Med., 43(6):828-36 (2000).

(56) References Cited

OTHER PUBLICATIONS

Ma et al., Asymmetric dipolar cycloaddition reactions: a practical, convergent synthesis of chiral pyrrolidines, Tetrahedron: Asymmetry, 8(6):883-8 (1997).
Ma et al., Voxel-by-voxel functional diffusion mapping for early evaluation of breast cancer treatment, Inf. Process. Med. Imaging, 21:276-87 (2009).
Macdonald et al., Response criteria for phase II studies of supratentorial malignant glioma, J. Clin. Oncol., 8(7):1277-80 (1990).
Magnetic Resonance Imaging, two pages, Churchill Livingstone's Dictionary of Nursing (2006).
Matsuoka et al., Quantitative assessment of air trapping in chronic obstructive pulmonary disease using inspiratory and expiratory volumetric MDCT, AJR Am. J. Roentgenol., 190(3):762-9 (2008).
Matsuoka et al., Quantitative assessment of peripheral airway obstruction on paired expiratory/inspiratory thin-section computed tomography in chronic obstructive pulmonary disease with emphysema, J. Comput. Assist. Tomogr., 31(3):384-9 (2007).
Mattiello et al., The b matrix in diffusion tensor echo-planar imaging, Magn. Reson. Med., 37(2):292-300 (1997).
McCubrey et al., Emerging Raf inhibitors, Expert Opin. Emerg. Drugs, 14(4):633-48 (2009).
Mehta et al., Monitoring radiographic brain tumor progression, Toxins (Basel), 3(3):191-200 (2011).
Meyer et al., A methodology for registration of a histological slide and in vivo MRI volume based on optimizing mutual information, Mol. Imaging, 5(1):16-23 (2006).
Meyer et al., Demonstration of accuracy and clinical versatility of mutual information for automatic multimodality image fusion using affine and thin-plate spline warped geometric deformations, Med. Image Anal., 1(3):195-206 (1997).
Mirzoeva et al., Basal subtype and MAPK/ERK kinase (MEK)-phosphoinositide 3-kinase feedback signaling determine susceptibility of breast cancer cells to MEK inhibition, Cancer Res., 69(2):565-72 (2009).
Moffat et al., Diffusion imaging for evaluation of tumor therapies in preclinical animal models, MAGMA, 17(3-6):249-59 (2004).
Moffat et al., Diffusion MR imaging in adult neoplasia, CUP, Cambridge: Physiological MR in Clinical Neuroscience, (2004).
Moffat et al., Functional diffusion map: a noninvasive MRI biomarker for early stratification of clinical brain tumor response, Proc. Natl. Acad. Sci. USA, 102(15):5524-9 (2005).
Moffat et al., The functional diffusion map: an imaging biomarker for the early prediction of cancer treatment outcome, Neoplasia, 8(4):259-67 (2006).
Montagut et al., Targeting the RAF-MEK-ERK pathway in cancer therapy, Cancer Lett., 283(2):125-34 (2009).
Muhlradt et al., Epothilone B stabilizes microtubuli of macrophages like taxol without showing taxol-like endotoxin activity, Cancer Res., 57(16):3344-6 (1997).
Nakano et al., Computed tomographic measurements of airway dimensions and emphysema in smokers. Correlation with lung function, Am. J. Respir. Crit. Care Med., 162(3 Pt. 1):1102-8 (2000).
Nicolaou et al., Synthesis of epothilones A and B in solid and solution phase, Nature, 387(6630):268-72 (1997).
O'Connor et al., DCE-MRI biomarkers in the clinical evaluation of antiangiogenic and vascular disrupting agents, Br. J. Cancer, 96:189-95 (2007).
Ostergaard et al., High resolution measurement of cerebral blood flow using intravascular tracer bolus passages, Part I: Mathematical approach and statistical analysis, Magn. Reson. Med., 36:715-25 (1996).
Ozcan et al., Characterization of imaging gradients in diffusion tensor imaging, J. Magn. Reson., 207(1):24-33 (2010).
Padhani et al., Diffusion-weighted magnetic resonance imaging as a cancer biomarker: consensus and recommendations, Neoplasia, 11(2):102-25 (2009).
Panda et al., Differential effects of vinblastine on polymerization and dynamics at opposite microtubule ends, J. Biol. Chem., 271 (47):29807-12 (1996).
Panda et al., Stabilization of microtubule dynamics by estramustine by binding to a novel site in tubulin: a possible mechanistic basis for its antitumor action, Proc. Natl. Acad. Sci. USA, 94(20):10560-4 (1997).
Park et al., Registration methodology for histological sections and ex vivo imaging of human prostate, Academic Radiology, 15(8) (Aug. 2008).
Pelizzari et al., Three dimensional correlation of PET, CT and MRI images, J. Nucl. Med., 28(4):682-3 (1987).
Petrylak et al., Docetaxel and estramustine compared with mitoxantrone and prednisone for advanced refractory prostate cancer, N. Engl. J. Med., 351 (15):1513-20 (2004).
Poulikakos et al., RAF inhibitors transactivate RAF dimers and ERK signalling in cells with wild-type BRAF, Nature, 464(7287):427-30 (2010).
Preusser et al., Current concepts and management of glioblastoma, Ann. Neurol., 70(1):9-21 (2011).
Regan et al., Genetic epidemiology of COPD (COPDGene) study design, COPD, 7(1):32-43 (2010).
Rehemtulla et al., Molecular imaging of gene expression and efficacy following adenoviral-mediated brain tumor gene therapy, Mol. Imaging, 1(1):43-55 (2002).
Reinhardt et al., Registration-based estimates of local lung tissue expansion compared to xenon CT measures of specific ventilation, Med. Image Anal., 12(6):752-63 (2008).
Reinhardt et al., Registration-derived estimates of local lung expansion as surrogates for regional ventilation, Int. Process. Med. Imaging, 20:763-74 (2007).
Reischauer et al., Bone metastases from prostate cancer: assessing treatment response by using diffusion-weighted imaging and functional diffusion maps—initial observations, Radiology, 257(2):523-31 (2010).
Robson, Non-linear gradients on clinical MRI systems introduce systematic errors in ADC and DTI measurements, ISMRM Proceedings (2002).
Rodrigues et al., The C-neu mammary carcinoma in Oncomice; characterization and monitoring response to treatment with herceptin by magnetic resonance methods, MAGMA, 17(3-6):260-70 (2004).
Romeo et al., Magnet field profiling: analysis and correcting coil design, Magn. Reson. Med., 1(1):44-65 (1984).
Rosen et al., Perfusion imaging with NMR contrast agents, Magn. Reson. Med., 14:249-65 (1990).
Ross et al. Assessment of the functional diffusion map: an imaging biomarker for early stratification of glioma clinical response, 2006 ASCO Annual Meeting Journal of Clinical Oncology, 24(18s): 1518 (2006).
Ross et al., Contributions of cell kill and posttreatment tumor growth rates to the repopulation of intracerebral 9L tumors after chemotherapy: an MRI study, Proc. Natl. Acad. Sci. USA, 95(12):7012-7 (1998).
Ross et al., Evaluation of cancer therapy using diffusion magnetic resonance imaging, Mol. Cancer Ther., 2(6):581-7 (2003).
Ross et al., Magnetic resonance imaging in cancer research, Eur. J. Cancer, 38(16):2147-56 (2002).
Ross et al., The role of magnetic resonance in the evaluation of cancer therapeutics, Clin. Cancer Res., 5:3870s-1s (1999).
Roth et al., High-b-value diffusion-weighted MR imaging for pretreatment prediction and early monitoring of tumor response to therapy in mice, Radiology, 232(3):685-92 (2004).
Sawyers, Imatinib GIST keeps finding new indications: successful treatment of dermatofibrosarcoma protuberans by targeted inhibition of the platelet-derived growth factor receptor, J. Clin. Oncol., 20(17):3568-9 (2002).
Schepkin et al., Proton and sodium MRI assessment of emerging tumor chemotherapeutic resistance, NMR Biomed., 19(8):1035-42 (2006).
Scher et al., Prostate cancer clinical trial end points: "RECIST"ing a step backwards, Clin. Cancer Res., 11(14):5223-32 (2005).
Scher et al., The association between measures of progression and survival in castrate-metastatic prostate cancer, Clin. Cancer Res., 13(5):1488-92 (2007).
Sebolt-Leopold et al., Targeting the mitogen-activated protein kinase cascade to treat cancer, Nat. Rev. Cancer, 4(12):937-47 (2004).

(56) References Cited

OTHER PUBLICATIONS

Sebolt-Leopold, Advances in the development of cancer therapeutics directed against the RAS-mitogen-activated protein kinase pathway, Clin. Cancer Res., 14(12):3651-6 (2008).

Shimizu et al., The clinical effect of the dual-targeting strategy involving PI3K/AKT/mTOR and RAS/MEK/ERK pathways in patients with advanced cancer, Clin. Cancer Res., 18(8):2316-25 (2012).

Sos et al., Identifying genotype-dependent efficacy of single and combined PI3K- and MAPK- pathway inhibition in cancer, Proc. Natl. Acad. Sci. USA, 106(43):18351-6 (2009).

Stegman et al., Diffusion MRI detects early events in the response of a glioma model to the yeast cytosine deaminase gene therapy strategy, Gene Ther., 7(12):1005-10 (2000).

Taichman et al., The evolving biology and treatment of prostate cancer, J. Clin. Invest., 117)9):2351-61 (2007).

Tannock et al., Docetaxel plus prednisone or mitoxantrone plus prednisone for advanced prostate cancer, N. Engl. J. Med., 351(15):1502-12 (2004).

Therasse et al., New guidelines to evaluate the response to treatment in solid tumors. European Organization for Research and Treatment of Cancer, National Cancer Institute of the United States, National Cancer Institute of Canada, J. Natl. Cancer Inst., 92(3):205-16 (2000).

Thomas et al., Phase I study of the safety, tolerability, pharmacokinetics and pharmacodynamics of PTK787/ZK 222584 administered twice daily in patients with advanced cancer, J. Clin. Oncol., 23:4162-71 (2005).

Tofts et al., Estimating kinetic parameters from dynamic contrast-enhanced T(1)-weighted MRI of a diffusable tracer: standardized quantities and symbols, J. Magn. Reson. Imaging, 10:223-32 (1999).

Tofts, Modeling tracer kinetics in dynamic Gd-DTPA MR imaging, J. Magn. Reson. Imaging, 7:91-101 (1997).

Vasquez et al., Nanomolar concentrations of nocodazole alter microtubule dynamic instability in vivo and in vitro, Mol. Biol. Cell, 8(6):973-85 (1997).

Viola et al., Alignment by maximization of mutual information, in Proceedings of 5th Intl. Conf. on Computer Vision, MIT, IEEE Press 95CH35744:16-23 (1995).

Washko et al., Identification of early interstitial lung disease in smokers from the COPDGene Study, Acad. Radiol., 17(1):48-53 (2010).

Washko et al., Lung volumes and emphysema in smokers with interstitial lung abnormalities, N. Engl. J. Med., 364(10):897-906 (2011).

Watts et al., "Relationship Between Changes in BMD and Nonvertebral Fracture Incidence Associated with Risedronate: Reduction in risk of Nonvertebral Fracture is not Related to Change in BMD," J Bone Miner Res. 20:2097-104 (2005).

Wee et al., PI3K pathway activation mediates resistance to MEK inhibitors in KRAS mutant cancers, Cancer Res., 69(10):4286-93 (2009).

Wen et al., Updated response assessment criteria for high-grade gliomas: response assessment in neuro-oncology working group, J. Clin. Oncol., 28(11):1963-72 (2010).

Wilson et al., Radiofrequency thermal ablation: 3D MR histology correlation for localization of cell death in MR lesion images, in: Proceedings of Intl. Symp. Biomed. Imaging, pp. 1537-1540 (2004).

World Health Organization, WHO Handbook for Reporting Results of Cancer Treatment, World Health Organization Offset Publication, Atlanta (1979).

Wu et al., A method for calibrating diffusion gradients in diffusion tensor imaging, J. Comput. Assist. Tomogr., 31(6):984-93 (2007).

Xiong et al., A phase I surrogate endpoint study of SU68868 in patients with solid tumors, Invest. New Drugs, 22:459-66 (2004).

Yamashiro et al., Collapsibility of lung volume by paired inspiratory and expiratory CT scans: correlations with lung function and mean lung density, Acad. Radiol., 17(4):489-95 (2010).

Yim et al., Deformable lung registration between exhale and inhale CT scans using active cells in a combined gradient force approach, Med. Phys., 37(8):4307-17 (2010).

Yin et al., Mass preserving nonrigid registration of CT lung images using cubic B-spline, Med. Phys., 36(9):4213-22 (2009).

Yu et al., Response and determinants of cancer cell susceptibility to PI3K inhibitors: combined targeting of PI3K and Mek1 as an effective anticancer strategy, Cancer Biol. Ther., 7(2):307-15 (2008).

Zahra et al., Dynamic contrast-enhanced MRI as a predictor of tumour response to radiotherapy, Lancet Oncol., 8:63-74 (2007).

Zarow et al., A standardized method for brain-cutting suitable for both stereology and MRI-brain co-registration, J. Neurosci. Methods, 139(2):209-15 (2004).

Zhao et al., Early detection of treatment response by diffusion-weighted 1H-NMR spectroscopy in a murine tumour in vivo, Br. J. Cancer, 73(1):61-4 (1996).

\* cited by examiner

VOXEL-BASED APPROACH FOR DISEASE DETECTION AND EVOLUTION

CROSS-REFERENCE TO RELATED APPLICATIONS

This application claims priority to U.S. Provisional Application No. 61/563,333, entitled "Voxel-Based Approach for Disease Detection and Evolution," filed Nov. 23, 2011, which is hereby incorporated herein in their entirety.

STATEMENT OF GOVERNMENTAL INTEREST

This invention was made with government support under CA085878 awarded by the National Institutes of Health. The government has certain rights in the invention.

FIELD OF THE INVENTION

The present disclosure relates to novel and advantageous systems and methods for monitoring tissue regions and, more particularly, to systems and methods for determining or predicting changes in tissue regions over a period of time, for example, during patient diagnosis or treatment.

BACKGROUND

In current standard medical practice, imaging modalities are commonly used to rapidly acquire images to provide qualitative information on the state of a tissue or disease process. In clinical practice, these modalities provide information about the extent or presence of the disease via images that are visually assessed by a trained professional. While contrast information in the images is sensitive to the physiological state of the tissue as a result of disease, image contrasts are typically arbitrarily scaled and provide no quantitative information about the disease (e.g. cellularity, vasculature, functional, structural, volumetric or metabolism). Nevertheless, these imaging modalities are sensitive to changes provoked by a disease process and can be used to assess evolution and effects of treatment intervention of the disease by visual comparison of images acquired over time. However, the contrast changes in images taken over time may be difficult to detect by traditional qualitative visual assessment, even for the trained professional. Accordingly, a method for providing quantitative information about a disease over a period of time using imaging modalities is needed. Further, a method of providing one or more images of tissue taken over a period of time that is easier to accurately read than known methods of providing and/or comparing images is needed.

BRIEF SUMMARY OF THE INVENTION

The present disclosure relates to techniques for a computer-implemented method of analyzing a sample region of a body to predict the evolution of a disease. The method includes collecting, using a medical imaging device, a reference data set of a first sample region, the reference image data set comprising a first plurality of voxels each characterized by a signal value in the reference image data set. Further, the method includes collecting, using the medical imaging device, a second image data set of a second sample region, the second image data set comprising a second plurality of voxels each characterized by a signal value in the second image data set. After collection, the method includes registering via computer-executable instructions, the reference image data set and the second image data set to produce a co-registered image data set that comprises a plurality of co-registered voxels, wherein each of the co-registered voxels includes the signal value of the co-registered voxel of the reference image data set and the second image data set, and wherein each voxel includes the value of the difference between the co-registered voxel of the reference image data set and the second image data set. A threshold significance level for the value of the difference between the co-registered voxel of the reference image data set and the second image data set is determined and the volume of voxels that exceed the threshold significance level is quantified. The method finally includes forming a parametric response map via computer-executable instructions using the co-registered image data set and the threshold significance level for the value of the difference between the co-registered voxels to segment the parametric response map data into at least a region that exceeds the threshold significance level.

The present disclosure is also directed to an apparatus having a processor and a computer-readable medium that includes instructions that when executed by the processor cause the apparatus to collect, from a magnetic resonance imaging device, a plurality of fluid attenuated inversion recovery image (FLAIR) data sets of a sample region, wherein each image data set comprises a plurality of voxels, each of which is characterized by a signal value; register, in an image processing module of the apparatus, the plurality of image data sets to produce a co-registered image data set comprising a plurality of co-registered voxels, wherein each of the co-registered voxels includes the signal value from each of the plurality of image data sets; form, in a pathology diagnostic module of the apparatus, a parametric response map data set using the co-registered image data set, wherein the mapping data set comprises the changes in FLAIR signal values between the co-registered voxels; and perform, in the pathology diagnostic module, a threshold analysis of the mapping data set to segment the mapping data into at least one region where the change in the FLAIR signal values between the co-registered voxels was an increase.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive. In contrast, embodiments of methods described herein may improve the accuracy of the metric at diagnosing progression in the presence of tumor heterogeneity during treatment.

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the necessary fee.

While the specification concludes with claims particularly pointing out and distinctly claiming the subject matter that is regarded as forming the various embodiments of the present disclosure, it is believed that the disclosure will be better understood from the following description taken in conjunction with the accompanying Figures, in which:

DETAILED DESCRIPTION

Figure 1:
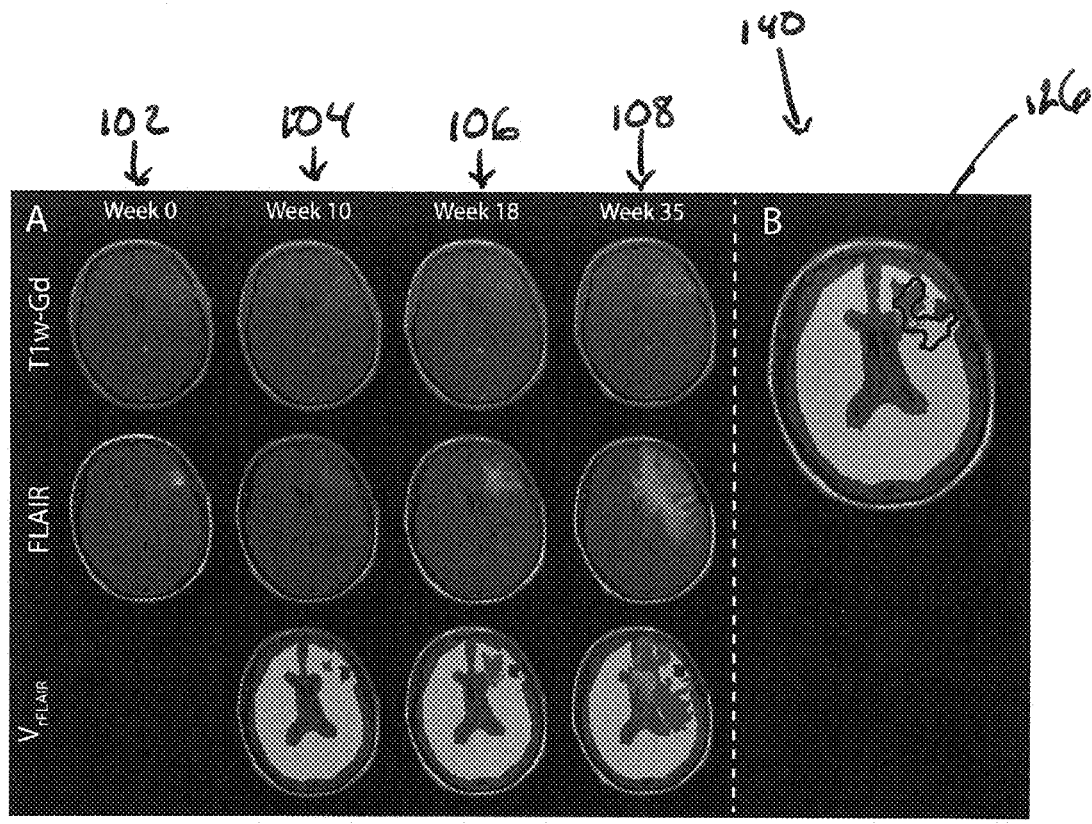
FIG. 1 illustrates a parametric response map, in accordance with embodiments of the present disclosure.

The present disclosure is directed to voxel-based analytical approach applied to conventional medical images to detect subtle changes in image contrast that are predictive of tissue/disease evolution. As earlier stated, while contrast information in traditional medical images may be sensitive to the physiological state of the imaged tissue as a result of disease, these image contrasts are typically arbitrarily scaled and provide no quantitative information about the disease (e.g. cellularity, vasculature, functional, structural, volumetric or metabolism). Nevertheless, these imaging modalities are sensitive to changes provoked by a disease process and can be used to assess evolution and effects of treatment intervention of the disease by visual comparison of images acquired over time.

The technology described herein is based on spatial alignment and appropriate intensity scaling of volumetric images acquired at two (or more) time points such that voxel-based quantitative analysis can be used to detect and display tissue regions undergoing early change as evidenced by changes in signal intensities contained within the images. While these image contrast changes are present in the original images resulting from known techniques, the images may be difficult to detect by traditional qualitative visual assessment, even for the trained professional. In contrast, the output of the present voxel-based analysis of the present disclosure provides stark labeling of regions suspected of the onset of change; and these regions have high probability to undergo gross change at a later date.

Normalization of these modalities is one approach to enhance sensitivity to physiological change for assessing disease extent serially as well as between patients. By identifying a region of tissue unaffected by disease and with a relatively constant physiological state for the time frame of interest (e.g. during treatment or for regular follow-up or annual scans), the signal intensity of this region can be used to normalize the entire three-dimensional (3D) image data set. As long as this normalizing region does not change substantially, any changes within the diseased tissue can be analyzed over time as well as between patients.

In one embodiment, the methods and systems of the present disclosure include normalization of cerebral blood volume ("CBV") to the CBV of white matter in the brain. The relative CBV (rCBV) can be accurately assessed and analyzed, thereby providing information on tumor grade that may be predictive of patient overall survival. Advantageously, embodiments of the present disclosure may use conventional non-quantitative (i.e., conventional "weighted") images that are normalized and subsequently analyzed. Prior to analysis, in some embodiments linear or deformable algorithms may be applied to the images to spatially align them, i.e., the images that are obtained at the different scan intervals are aligned with the reference image. Aligning the images (also referred to herein as "registration") allows for quantification of change on a voxel-by-voxel basis which can be used to provide a very sensitive approach to detect, quantify and spatially display changes in image contrasts to provide for detailed insight into the status, extent, progression and response of a disease using images obtained from a wide variety of imaging modalities, for example, but not limited to magnetic resonance imaging (MRI), computed tomography (CT), two-dimensional planar X-Ray, positron emission tomography (PET), ultrasound (US), optical imaging (i.e. fluorescence, near-infrared (NIR) & bioluminescence), and single-photon emission computed tomography (SPECT).

Within a given instrumentation source (e.g. MRI, CT, X-Ray, PET and SPECT) a variety of data can be generated. For example, MRI devices can generate diffusion, perfusion, permeability, normalized and spectroscopic images, which include molecules containing, for example, but not limited to, 1H, 13C, 23-Na, 31P, and 19F, hyperpolarized Helium, Xenon and/or 13C MRI, which can also be used to generate kinetic parameter maps. PET, SPECT and CT devices are also capable of generating static images as well as kinetic parameters by fitting temporally resolved imaging data to a pharmacokinetic model. Imaging data, irrespective of source and modality, can be presented as quantified (i.e., has physical units) or normalized (i.e., images are normalized to an external phantom or something of known and constant property or a defined signal within the image volume) maps so that images can be compared between patients as well as data acquired during different scanning sessions.

The techniques of the present disclosure are not limited to a particular type or kind of tissue region or motion. By way of example only, suitable tissue types include lung, prostate, breast, colon, rectum, bladder, ovaries, skin, liver, spine, bone, pancreas, cervix, lymph, thyroid, spleen, adrenal gland, salivary gland, sebaceous gland, testis, thymus gland, penis, uterus, trachea, skeletal muscle, smooth muscle, heart, etc. In some embodiments, the tissue region may be a whole body or large portion thereof (for example, a body segment such as a torso or limb; a body system such as the gastrointestinal system, endocrine system, etc.; or a whole organ comprising multiple tumors, such as whole liver) of a living human being. In some embodiments, the tissue region may be a diseased tissue region. In some embodiments, the tissue region may be an organ. In some embodiments, the tissue region may be a tumor, for example, a malignant or benign tumor. In some embodiments, the tissue region may be a breast tumor, a liver tumor, a bone lesion, and/or a head/neck tumor. In some embodiments the tissue may be from a non-human animal. In other embodiment the tissue may not be a tumor and/or may not be cancerous.

In addition, the techniques are not limited to a particular type or kind of treatment. In some embodiments, the techniques may be used as part of a pharmaceutical treatment, a vaccine treatment, a chemotherapy based treatment, a radiation based treatment, a surgical treatment, and/or a homeopathic treatment and/or a combination of treatments. In other embodiments the techniques may be used for prognosis, diagnosis, disease detection, staging, and treatment response assessment. Embodiments of the present disclosure may find application in, for example, but not limited to hospitals, clinics, clinical research organizations, research institutions and labs.

Parametric response maps ("PRM") were developed and shown to improve the sensitivity of diffusion-MRI data to aid in identifying early therapeutic response in glioma patients. PRM, when applied to diffusion-MRI data, had been validated as an early surrogate imaging biomarker for gliomas, head and neck cancer, breast cancer and metastatic prostate cancer to the bone, for example. PRM is found to improve the sensitivity of the diffusion and perfusion MRI data by classifying voxels based on the extent of change in the quantitative values over time. This approach provides not only spatial information and regional response in the cancer to treatment but is also a global measure that can be used as a decision making tool for the treatment management of cancer patients, for example. The global measure is presented as the relative volume of tumor whose quantitative values have increased, decreased or remained unchanged with time.

In known methods of analysis, images are interpreted subjectively based on image contrast, or quantitatively by lesion size, for example. In contrast, embodiments of the present disclosure may objectively depict the image contrast change over time in normal and diseased tissue for use as a potential surrogate indicator of disease evolution, for example, response or progression. In some embodiments, the method may include obtaining two or more volumetric images via an imaging modality; registering the image(s) to a reference image set; segmenting the voxel-by-voxel differences relative to a specified "significance threshold,"; quantifying the volume of voxels that exceed an established degree or amount of change; and/or producing colorized parametric response maps of one or more tissue regions that exhibit significant change. Embodiments of the present disclosure may include more, fewer, or different steps. In some embodiments, standard "non-quantitative" images such as standard MRI using conventional whole tissue/volume statistical approaches (for example, but not limited to mean, median, skewness, percentile, kurtosis, Kullback-Leibler, quantiles, standard deviation, etc.) may be used to create a parametric response map, after the images have been normalized in accordance with embodiments of the present disclosure.

Various voxel classification schemes are contemplated and within the spirit and scope of the present disclosure. In some embodiments, the classification scheme can include color-coded voxels of the processed images that form the PRM. For example, in some cases, the classification system may include color coded voxels representing an increase of a given parameter that may be colored red for example; a decrease in a given parameter that may be colored blue for example; and/or no change in a particular parameter that may be colored green for example. It will be understood that the color coding scheme could be any suitable color coding scheme and may employ any suitable or desirable colors. Further, in other embodiments, other systems for assigning a classification to individual voxels is possible, for example, instead of using colors, varying shades of gray may be used to denote different classifications; different geometric shapes could be used, for example open circles and closed circles, or any other suitable method for denoting differences between individual voxels on a parametric response map may be used. Additionally, more than three parameters may be signaled on a PRM on a voxel by voxel basis. For example, instead of red indicating an increase in a parameter, two or more different colors could be used, where each color indicates a set range of increase in the given parameter.

While some examples provided herein disclose the collection of two images, it is also contemplated and within the spirit and scope of the present disclosure, that multiple images may be collected and used to generate a PRM.

The image data may be collected from an external imaging system in communication with a processor-based PTM system, e.g., connected through wired or wireless connections. In other examples, the PRM system may be embedded with a medical imaging system, for example a CT system, MRI system, etc. An example computer system for executing the PRM techniques described herein is provided in FIG. 3 discussed further below.

Generally, the PRM system includes an image collector engine that receives and stores the medical images and a deformation registration engine that takes the images and performs a linear or deformable registration of serial images. The deformation registration engine provides a set of tissue specific parameters for tailoring the engine to register images of that tissue, where these parameters may represent physical characteristics of the tissue (e.g., general shape, position, expected volume, changes between physiological states, swelling due to edema, in the case of muscle tissue deformation due to contraction or atrophy and or changes in tissue due to tissue strain and elasticity tests to assess distensibility). The image registration can be achieved using nonlinear deformable algorithms in some embodiments to provide for higher degrees of freedom needed to align the images together. In examples where tissue volume or position changes occur between serial medical images, deformation may be performed as part of the registration, which includes scaling of at least one image data or portions thereof.

After registration, a voxel analysis engine examines the combined, registered image data from the registration engine, to perform a classification on the image data. The analysis engine, for example, determines signal intensity change across medical images on a voxel-by-voxel basis for the image data. The size of the region-of-interest (ROI) may be determined manually, e.g., by contouring over the analyzed tissue, or may be generated automatically by the medical imaging system, or in other embodiments may be determined by a combination of manual and automatic techniques. In addition to determining signal intensity changes within each voxel, the analysis engine can also identify the relative volumes of the signal changes and the location of the changed and the unchanged voxels. While conventional ways of measuring registered data sets can be used, e.g., the mean of the Jacobian or dissimilarity measures based on the histograms of the CT images where information from the measure is pooled throughout the tissue of interest into a single outcome measure, the measurements forfeit spatial information. Each individual voxel is a volume in 3D space that corresponds to a location in the tissue. Therefore, in some embodiments, the analysis engine retains the spatial information by classifying voxels into discrete groups that can be analyzed as a global metric, for example.

In some embodiments, the voxel analysis engine is configured to perform tissue analysis on only a portion of the registered image data, for example, a particular tissue region or tissue sub-type. In such examples, the analysis engine may perform image isolation to filter out image data not corresponding to the tissue region or sub-type of interest. The registration process of the present disclosure in some embodiments may be accomplished automatically, manually, or may be a combination of automatic and manual processes.

In some embodiments, the methods disclosed herein may be used to predict tissue or disease evolution of people with brain tumors based upon detected and quantified changes in MRI fluid attenuated inversion recovery imaging (FLAIR) and contrast-enhanced (Gd-DTPA) T1-weighted images. Therapeutic management (diagnostic, surgical, postoperative, and post-therapeutic stages) of tumors and especially of gliomas remains a challenge. Even with advancements in the clinical management of cancer patients, assessment of recurrence in tumors with their inherent heterogeneous enhancement, growth patterns and irregular nature, continues to be difficult to assess. The standard clinical practice for evaluating progression relies on late or serial changes in traditional non-volumetric tumor measurements performed using images acquired on CT or MRI. With new efficacious treatment options being developed, there is a critical need for a quick and accurate method for determining tumor progression.

Gliomas continue to be the most common form of brain malignancy in adult patients. Monitoring glioma changes by MRI is now the technique of first choice for assessing therapeutic response and recurrence. Lately, new standardized glioma response to treatment criteria have been published by the Response Assessment in Neuro-Oncology Working Group (RANO). These new criteria took a step forward compared to the previous standard-of-care (MacDonald's criteria) by using in addition to the anatomical T1-weighted post contrast images (CE-T1w), a secondary endpoint based on changes in the fluid attenuated inversion recovery images (FLAIR) to delineate brain tumor. RANO recommendations highlight the fact that future developments of new early imaging biomarkers will be highly conditioned by both: (i) the development and the integration of new images to monitor the physiological response of gliomas to therapies; and (ii) the implementation of new tools to analyze, quantify and interpret not only one, but multiple MR parameters (anatomical and/or physiological) simultaneously.

Quantitative imaging has been shown to compliment standard anatomical imaging techniques. Although promising as a surrogate biomarker of recurrence, monitoring the percent change of a metric obtained through whole-tumor summary statistics (e.g. mean and median values) continues to be the standard approach for evaluating the efficacy of quantitative MR metrics as biomarkers of therapeutic response. Although this technique has been successfully used in oncology, it has limitations. An important limit of this approach is that the mean value cannot quantify heterogeneities present in gliomas on MR images, and as such attenuates the sensitivity of the metric at identifying tumor recurrence. In contrast, embodiments of methods described herein may to improve the accuracy of the metric at diagnosing progression in the presence of tumor heterogeneity during treatment. In addition, this method is applicable to imaging techniques commonly used for assessing progression by volumetric and non-volumetric changes in tumors.

EXAMPLE

Methods of the present disclosure were demonstrated in a cohort of 14 glioma patients and compared to standard MRI-based criteria of clinical progression. The fourteen patients with pathologically proven grade III/IV gliomas were enrolled on a protocol of intra-treatment MRI. MRI scans were performed before and during treatment (every 2 months) until tumor recurrence was identified by Macdonald Criteria. All images were acquired on 1.5T or 3T MRI scanners. The MR1 protocol included fluid-attenuated inversion recovery imaging (FLAIR) and contrast-enhanced (Gd-DTPA) T1-weighted imaging. To avoid variability between scanners, subjects used the original scanner for all subsequent scans.

Subsequent to voxel-based analysis, FLAIR images were normalized to the mean signal intensity of white matter tracks (rFLAIR). All image data was registered to pre-treatment Gd-enhanced T1-weighted images using mutual information as an objective function and Nelder-Mead simplex as an optimizer. Automatic registration of different and similar-weighted serial MRI scans for the same patient was performed assuming a rigid-body geometry relationship. Following registration, brain tumors VO1s were manually contoured by a neuro-radiologist over the enhancing region of the tumor on the Gd-enhanced T1-weighted images.

Voxel-based analysis was accomplished by collating the difference between the rFLAIR ($\Delta$rFLAIR=rFLAIR($t_i$)-T1 ($t_{i-1}$), (where t is time and i is an index) for each voxel within the whole brain volume at each longitudinal follow-up scan using the baseline as the subtrahend. Baseline was defined as either the pre-treatment or subsequent rFLAIR image. Individual voxels were stratified into three categories based on the change of rFLAIR relative to baseline rFLAIR maps. Red voxels represented volume within the brain where rFLAIR value increased beyond a predetermined user-defined $\Delta$rFLAIR threshold; blue voxels represent volumes whose rFLAIR decreased by more than the defined threshold; and the green voxels represent voxels within the tumor that were unchanged (that is, the absolute value of $\Delta$rFLAIR was within the defined thresholds of significant change). Disease recurrence was defined by voxel-based metrics as the sum of red voxels that exceed a percentage, (i.e. here tested at 20%), of the tumor volume as delineated on T1w-Gd.

FIG. 1 illustrates a temporal MRI series from a representative chemo-RT treated GBM patient at baseline 102 and follow-up 104, 106, 108 scan dates. Disease progression was determined on week 35 by the Macdonald criteria. The regions of increased rFLAIR are in red. Red regions correspond to eventual progressive tumor as shown at 140. The area of increased rFLAIR was detected on week 18 (shown as volume of red voxels (VrFLAIR+) 120 using pre-treatment rFLAIR as baseline), 23 weeks prior to diagnosis by Macdonald criteria. In addition to the early diagnostic capabilities of this approach, regions of significant change as denoted red were found to correlate spatially with the pattern of tumor progression beyond the initial tumor site. In FIG. 1, the red region from this novel approach overlapped with most of the region designated recurrent tumor by T1w-Gd on week 35 (new tumor borders denoted by black line 126). This suggests that VrFLAIR+ (red voxels) found outside the tumor T1w-Gd regions reveals the spatial location of newly forming tumor beyond the initial site of malignancy 140.

Figure 2:
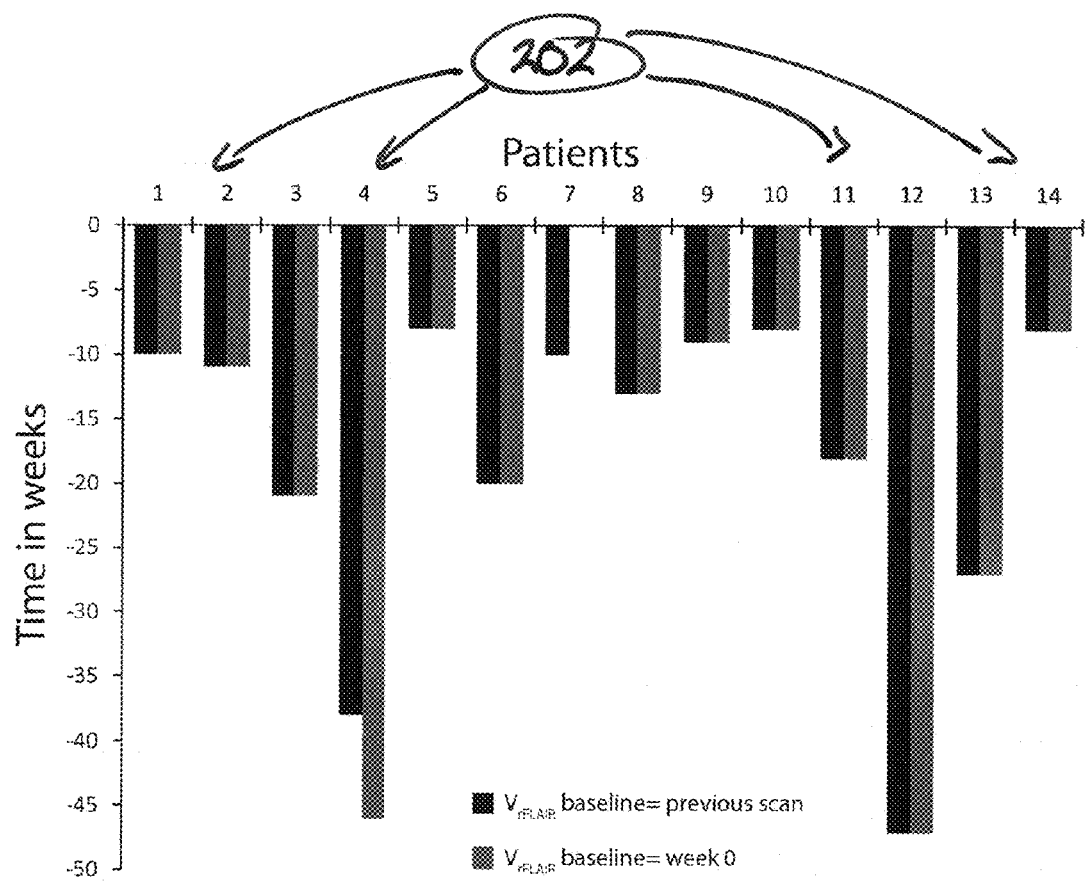
FIG. 2 provides a graph showing how much faster methods of the present disclosure are at assessing tumor recurrence versus known methods, in accordance with embodiments of the present disclosure.

FIG. 2 is a plot of the difference in the time of tumor recurrence as determined by VrFLAIR and Macdonald criteria for each patient 202. Large variations in the difference in time to diagnosis were observed between patients. Nevertheless, diagnosis of tumor recurrence by VrFLAIR always preceded Macdonald. On average, VrFLAIR was able to diagnose tumor recurrence as early as 18±3 weeks (SEM) prior to the Macdonald criteria. In two of these cases, tumor recurrence was identified 40 weeks (10 months) before the standard assessment criteria. Assessment of the different baselines when using this technology revealed little difference in the sensitivity of this technique. Recurrence was identified in over 90% of patients when using the pre-treatment rFLAIR as baseline for the new method. When using the previous scan, recurrence was identified in all patients.

These results show that the voxel-based PRM approach of embodiments of the present disclosure provide for the early detection and spatial depiction of brain tumor progression prior to detection by currently available conventional MRI-based criteria.

While embodiments have been described with regard to use for determining and/or predicting the evolution of brain tumors, other extensions of this invention include applications using many other "weighted" image data types, such as, but not limited to T1, T2, proton density images, FLAIR and STIR (inversion recovery pulses), metabolite-specific images, pulsed gradient spin echo images (PGSE), oscillating gradient spin echo (OGSE) etc. for MRI that when normalized are used to monitor changes associated from a multitude of disease types and across all tissue types over time. Normalized data generated from other medical imaging devices (e.g. optical, CT, X-Ray, PET and SPECT) are also applicable.

Example PCM System

Figure 3:
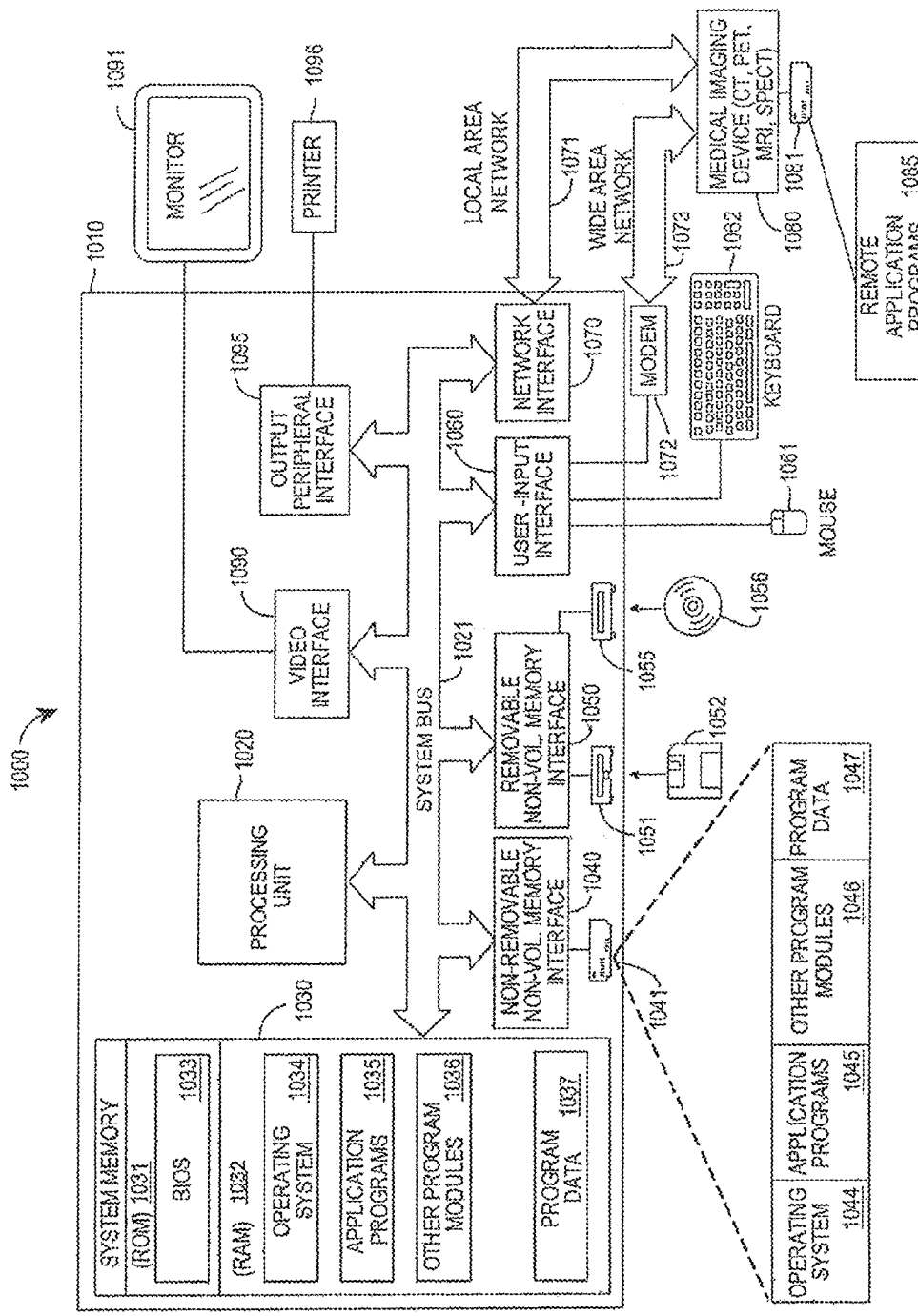
FIG. 3 is a schematic of a representative system for use with embodiments with the present disclosure.

FIG. 3 is a block diagram of an example computer system 1000 on which a PRM system may operate, in accordance with the described embodiments. The computer system 1000 may be a PRM system, for example. The computer system 1000 includes a computing device in the form of a computer 1010 that may include, but is not limited to, a processing unit 1020, a system memory 1030, and a system bus 1021 that couples various system components including the system memory to the processing unit 1020. The system bus 1021 may be any of several types of bus structures including a memory bus or memory controller, a peripheral bus, and a local bus using any of a variety of bus architectures. By way of example, and not limitation, such architectures include the Industry Standard Architecture (ISA) bus, Micro Channel Architecture (MCA) bus, Enhanced ISA (EISA) bus, Video Electronics Standards Association (VESA) local bus, and Peripheral Component Interconnect (Pa) bus (also known as Mezzanine bus).

Computer 1010 typically includes a variety of computer readable media. Computer readable media can be any available media that can be accessed by computer 1010 and includes both volatile and nonvolatile media, and both removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 1010. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above are also included within the scope of computer readable media.

The system memory 1030 includes computer storage media in the form of volatile and/or nonvolatile memory such as read only memory (ROM) 1031 and random access memory (RAM) 1032. A basic input/output system 1033 (BIOS), containing the basic routines that help to transfer information between elements within computer 1010, such as during start-up, is typically stored in ROM 1031. RAM 1032 typically contains data and/or program modules that are immediately accessible to and/or presently being operated on by processing unit 1020. By way of example, and not limitation, F*igure* 24 illustrates operating system 1034, application programs 1035, other program modules 1036, and program data 1037.

The computer 1010 may also include other removable/non-removable, volatile/nonvolatile computer storage media. By way of example only, F*igure* 24 illustrates a hard disk drive 1041 that reads from or writes to non-removable, nonvolatile magnetic media, a magnetic disk drive 1051 that reads from or writes to a removable, nonvolatile magnetic disk 1052, and an optical disk drive 1055 that reads from or writes to a removable, nonvolatile optical disk 1056 such as a CD ROM or other optical media.

Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1041 is typically connected to the system bus 1021 through a non-removable memory interface such as interface 1040, and magnetic disk drive 1051 and optical disk drive 1055 are typically connected to the system bus 1021 by a removable memory interface, such as interface 1050.

The drives and their associated computer storage media discussed above and illustrated in FIG. 3 provide storage of computer readable instructions, data structures, program modules and other data for the computer 810. In FIG. 3, for example, hard disk drive 1041 is illustrated as storing operating system 1044, application programs 1045, other program modules 1046, and program data 1047. Note that these components can either be the same as or different from operating system 1034, application programs 1035, other program modules 1036, and program data 1037. Operating system 1044, application programs 1045, other program modules 1046, and program data 1047 are given different numbers here to illustrate that, at a minimum, they are different copies. A user may enter commands and information into the computer 1010 through input devices such as a keyboard 1062 and cursor control device 1061, commonly referred to as a mouse, trackball or touch pad. A monitor 1091 or other type of display device is also connected to the system bus 1021 via an interface, such as a graphics controller 1090. In addition to the monitor, computers may also include other peripheral output devices such as printer 1096, which may be connected through an output peripheral interface 1095.

The computer 1010 may operate in a networked environment using logical connections to one or more remote computers, such as a remote computer 1080. The remote computer 1080 may be a personal computer, a server, a router, a network PC, a peer device or other common network node, and typically includes many or all of the elements described above relative to the computer 1010, although only a memory storage device 1081 has been illustrated in FIG. 3. The logical connections depicted in F*igure* 24 include a local area network (LAN) 1071 and a wide area network (WAN) 1073, but may also include other networks. Such networking environments are commonplace in hospitals, offices, enterprise-wide computer networks, intranets and the Internet. In the illustrated example, the remote computer 1080 is a medical imaging device, such as a CT scanning device, PET scanning device, MRI device, SPECT device, etc. While a single remote computer 1080 is shown, the LAN 1071 and/or WAN 1073 may be connected to any number of remote computers. The remote computers may be independently functioning, for example, where the computer 1010 serves as a master and a plurality of different slave computers (e.g., each functioning as a different medical imaging device), are coupled thereto. In such centralized environments, the computer 1010 may provide one or both of an image processing module and a tissue classification diagnostic module for a group of remote processors, where the image processing module may include an image collector engine and a deformation registration engine and the tissue classification diagnostic module may include a voxel analysis engine. In other examples, the computer 1010 and a plurality of remote computers operate in a distributed processing manner, where imaging processing module and tissue classification diagnostic module are performed in a distributed manner across different computers. In some embodiments, the remote computers 1080 and the computer 1010 may be part of a "cloud" computing environment, over the WAN 1073, for example, in which image processing and tissue classification diagnostic services are the result of shared resources, software, and information collected from and push to each of the computers. In this way, the remote computers 1080 and the computer 1010 may operate as terminals to access and display data, including tissue classification diagnostics (tissue phasic classification), delivered to the computers through the networking infrastructure and more specifically shared network resources forming the "cloud."

It is noted that one or more of the remote computers 1080 may function as a remote database or data center sharing data to and from the computer 1010.

When used in a LAN networking environment, the computer 1010 is connected to the LAN 1071 through a network interface or adapter 1-70. When used in a WAN networking environment, the computer 1010 typically includes a modem 1072 or other means for establishing communications over the WAN 1073, such as the Internet. The modem 1072, which may be internal or external, may be connected to the system bus 1021 via the input interface 1060, or other appropriate mechanism. In a networked environment, program modules depicted relative to the computer 1010, or portions thereof, may be stored in the remote memory storage device 1081. By way of example, and not limitation, FIG. 3 illustrates remote application programs 1085 as residing on memory device 1081. The communications connections 1070, 1072 allow the device to communicate with other devices. The communications connections 1070, 1072 are an example of communication media.

The methods for analyzing a sample region of a body to determine the state of the tissue (which may include analyzing tissue for the purpose of diagnosis, assessing pathology, assessing response to treatment, etc.) described above may be implemented in part or in their entirety using one or more computer systems such as the computer system 1000 illustrated in FIG. 3.

Some or all calculations performed in the tissue characterization determination may be performed by a computer such as the computer 1010, and more specifically may be performed by a processor such as the processing unit 1020, for example. In some embodiments, some calculations may be performed by a first computer such as the computer 1010 while other calculations may be performed by one or more other computers such as the remote computer 1080, as noted above. The calculations may be performed according to instructions that are part of a program such as the application programs 1035, the application programs 1045 and/or the remote application programs 1085, for example. Such functions including, (i) collecting image data from a medical imaging device, either connected remotely to the device or formed as part of the computer system 100; (ii) rigid-body and/or deformably registering, in an image processing module, such collected image data to produce a co-registered image data comprising a plurality of voxels; (iii) determining, in the image processing module, changes in signal values for each of the plurality of voxels for the co-registered image data between a first phase state and the second phase state; (iv) forming, in a tissue state diagnostic module, a tissue classification mapping data of the changes in signal values from the co-registered image data, wherein the mapping data includes the changes in signal values segmented by the first phase state and the second phase state; (v) performing, in the tissue state diagnostic module, a threshold analysis of the mapping data to segment the mapping data into at least one region indicating the presence of the tissue state condition and at least one region indicating the non-presence of the tissue state condition; and (vi) analyzing the threshold analysis of the mapping data to determine the presence of the tissue state condition in the sample region.

Relevant data may be stored in the ROM memory 1031 and/or the RAM memory 1032, for example. In some embodiments, such data is sent over a network such as the local area network 1071 or the wide area network 1073 to another computer, such as the remote computer 1081. In some embodiments, the data is sent over a video interface such as the video interface 1090 to display information relating to the tissue state condition to an output device such as, the monitor 1091 or the printer 1096, for example. In other examples, the data is stored on a disc or disk drive, such as 856 or 852, respectively.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments for purposes of illustration only. One skilled in the art will readily recognize from the discussion herein that alternative embodiments of the structures and methods illustrated herein may be employed without departing from the principles described herein.

Upon reading this disclosure, those skilled in the art will appreciate still additional alternative structural and functional designs for a system and a process for identifying terminal road segments through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented method of analyzing a sample region of a body to predict the evolution of a disease, the method comprising:
    collecting, using a magnetic resonance imaging (MRI) medical imaging device, a weighted reference image data set of a brain tumor taken at a first time point, the weighted reference image data set comprising a first plurality of voxels each characterized by a signal value in the reference image data set;
    collecting, using the MRI medical imaging device, a weighted second image data set of the brain tumor taken at a time after the first time point, the weighted second image data set comprising a second plurality of voxels each characterized by a signal value in the second image data set;
    normalizing the weighted reference image set to a tissue or a structure in the brain tumor taken at the first time point, and normalizing the weighted second image data set to a tissue or a structure in the brain tumor taken at a time after the first time point;
    registering via computer-executable instructions, the normalized reference image data set and the normalized second image data set to produce a co-registered image data set that comprises a plurality of co-registered voxels, wherein each of the co-registered voxels includes the signal value of the co-registered voxel of the reference image data set and the second image data set, and wherein each of the co-registered voxels includes the value of the difference between the co-registered voxel of the reference image data set and the second image data set;
    determining a threshold significance level for the value of the difference between the co-registered voxel of the reference image data set and the second image data set;
    quantifying the volume of voxels that exceed the threshold significance level;
    forming a parametric response map via computer-executable instructions using the co-registered image data set and the threshold significance level for the value of the difference between the co-registered voxels to segment the parametric response map data into at least a region that exceeds the threshold significance level; and
    establishing a disease growth rate percentage, whereby if the quantity of the co-registered voxels that exceed the threshold significance level is greater than the established disease growth rate percentage, the tumor is determined to be recurring, wherein the disease growth rate percentage is a percentage of the whole volume tumor.

2. The method of claim 1, where the weighted reference image data set and the weighted second image data set are collected as T1 images.

3. The method of claim 1, where the weighted reference image data set and the weighted second image data set are collected as T2 images.

4. The method of claim 1, where the weighted reference image data set and the weighted second image data set are collected as proton density images.

5. The method of claim 1, where the weighted reference image data set and the weighted second image data set are collected as short inversion time inversion recovery (STIR) images.

6. The method of claim 1, wherein registering the normalized reference image data set and the normalized second image data set comprises applying an image segmentation to the reference image and the second image.

7. The method of claim 1, further comprising quantifying the number of co-registered voxels that are less than the threshold significance level and segmenting the parametric response map into a region that includes voxels that are less than the threshold significance level.

8. The method of claim 1, further comprising quantifying the number of co-registered voxels that are equal to the threshold significance level and segmenting the parametric response map into a region that includes voxels that are equal to the threshold significance level.

9. A computer-implemented method of analyzing a sample region of a body to predict the evolution of a disease, the method comprising:
    collecting, using a magnetic resonance imaging (MRI) medical imaging device, a weighted reference image data set of a brain tumor taken at a first time point, the weighted reference image data set comprising a first plurality of voxels each characterized by a signal value in the reference image data set;
    collecting, using the MRI medical imaging device, a weighted second image data set of the brain tumor taken at a time after the first time point, the weighted second image data set comprising a second plurality of voxels each characterized by a signal value in the second image data set;
    normalizing the weighted reference image data set to a tissue or a structure in the brain tumor taken at the first time point, and normalizing the weighted second image data set to a tissue or a structure in the brain tumor taken at a time after the first time point;
    registering via computer-executable instructions, the normalized reference image data set and the normalized second image data set to produce a co-registered image data set that comprises a plurality of co-registered voxels, wherein each of the co-registered voxels includes the signal value of the co-registered voxel of the reference image data set and the second image data set, and wherein each of the co-registered voxels includes the value of the difference between the co-registered voxel of the reference image data set and the second image data set;
    determining a threshold significance level for the value of the difference between the co-registered voxel of the reference image data set and the second image data set;
    quantifying the volume of voxels that exceed the threshold significance level;
    forming a parametric response map via computer-executable instructions using the co-registered image data set and the threshold significance level for the value of the difference between the co-registered voxels to segment the parametric response map data into at least a region that exceeds the threshold significance level; and
    establishing a disease growth rate percentage of 20 percent, whereby if the quantity of the co-registered voxels that exceed the threshold significance level is greater than the established disease growth rate of 20 percent, the tumor is determined to be recurring, wherein the disease growth rate percentage is a percentage of the whole volume tumor.

10. The method of claim 9, where the weighted reference image data set and the weighted second image data set are collected as T1 images.

11. The method of claim 9, where the weighted reference image data set and the weighted second image data set are collected as T2 images.

12. The method of claim 9, where the weighted reference image data set and the weighted second image data set are collected as proton density images.

13. The method of claim 9, where the weighted reference image data set and the weighted second image data set are collected as short inversion time inversion recovery (STIR) images.

14. The method of claim 9, wherein registering the normalized reference image data set and the normalized second image data set comprises applying an image segmentation to the reference image and the second image.

15. The method of claim 9, further comprising quantifying the number of co-registered voxels that are less than the threshold significance level and segmenting the parametric response map into a region that includes voxels that are less than the threshold significance level.

16. The method of claim 9, further comprising quantifying the number of co-registered voxels that are equal to the threshold significance level and segmenting the parametric response map into a region that includes voxels that are equal to the threshold significance level.

* * * * *